United States Patent [19]
Ono

[11] 4,309,903
[45] Jan. 12, 1982

[54] METHOD AND APPARATUS FOR ANALYZING SELECTED MATERIAL PROPERTIES WITH MAGNETOMECHANICAL ACOUSTIC EMISSIONS

[75] Inventor: Kanji Ono, Granada HIlls, Calif.

[73] Assignee: The Regents of the University of California, Berkeley, Calif.

[21] Appl. No.: 107,313

[22] Filed: Dec. 26, 1979

[51] Int. Cl.³ .................. G01N 3/08; G01N 29/00; G01N 27/00

[52] U.S. Cl. ........................... 73/587; 73/659; 73/801

[58] Field of Search ............... 73/587, 801, 659

[56] References Cited

U.S. PATENT DOCUMENTS 4,064,735  12/1977  Hutchison et al. ............... 73/801 X

OTHER PUBLICATIONS

"Application of Correlation Analysis to Acoustic Emissions" by Ono et al., from Acoustic Emissions, ASTM STP 505, 1972, pp. 152-163.
"Acoustic Emission Behavior of Aluminum Alloys" by Ono et al., from Materials Evaluation, pp. 32-44, Feb. 1976.
"AE Characteristics and Stress Dependency of Magnetization Process . . . " by Kusanagi et al., published in The Proceedings of the First Nat'l Conference on Acoustic Emission," pp. 157-162, Dec. 1977, Tokyo.
"Identification of Acoustic Emission Source Mechanisms by Energy Spectrum Spectrum Analysis" by Woodward from Ultrasonics, Nov. 1976, pp. 249-255.
"Physical Acoustics Principles and Methods" by Mason et al., vol. XI, Chapter 6, Academic Press, 1975.
"Measurement of Residual Stress Using Magnetic Barkhausen Noise Analysis" by Matzkanin et al., Proceedings of ARPA/AFML Rev. of Quantitative NDE, 1-1976.

*Primary Examiner*—James J. Gill
*Attorney, Agent, or Firm*—Poms, Smith, Lande & Rose

[57] ABSTRACT

A method and apparatus for analyzing selected properties of a ferromagnetic material by magnetically inducing acoustic emissions in the material. The acoustic emission response is measured at a plurality of values of a selected response parameter, the response parameter being characterized by an acoustic emission response which, for each of its selected values, varies in mutual nonlinearity with the acoustic emission responses for the other selected values. The measured acoustic emission responses are compared to each other and to standard responses, thereby providing a more reliable measurement of the selected property than is attainable by analyzing at only one value of the response parameter. Comparing the ratio between acoustic emission responses at different values of the selected response parameter, with standard response ratios for the same response parameter values, further enhances reliability of the measurement.

In preferred embodiments the selected response parameter is the frequency of the acoustic emission response, the signal threshold level for obtaining an acoustic emission count rate, or the magnetic field strength. Properties selected for analysis in the preferred embodiments are stress, plastic deformation, microstructure and chemical composition.

The invention further includes structure in which transducers for measuring acoustic emission responses at different response parameter values are coupled to a specimen by a unitary coupling mechanism, thereby reducing spurious differences between the measurements at the various response parameter values.

27 Claims, 19 Drawing Figures

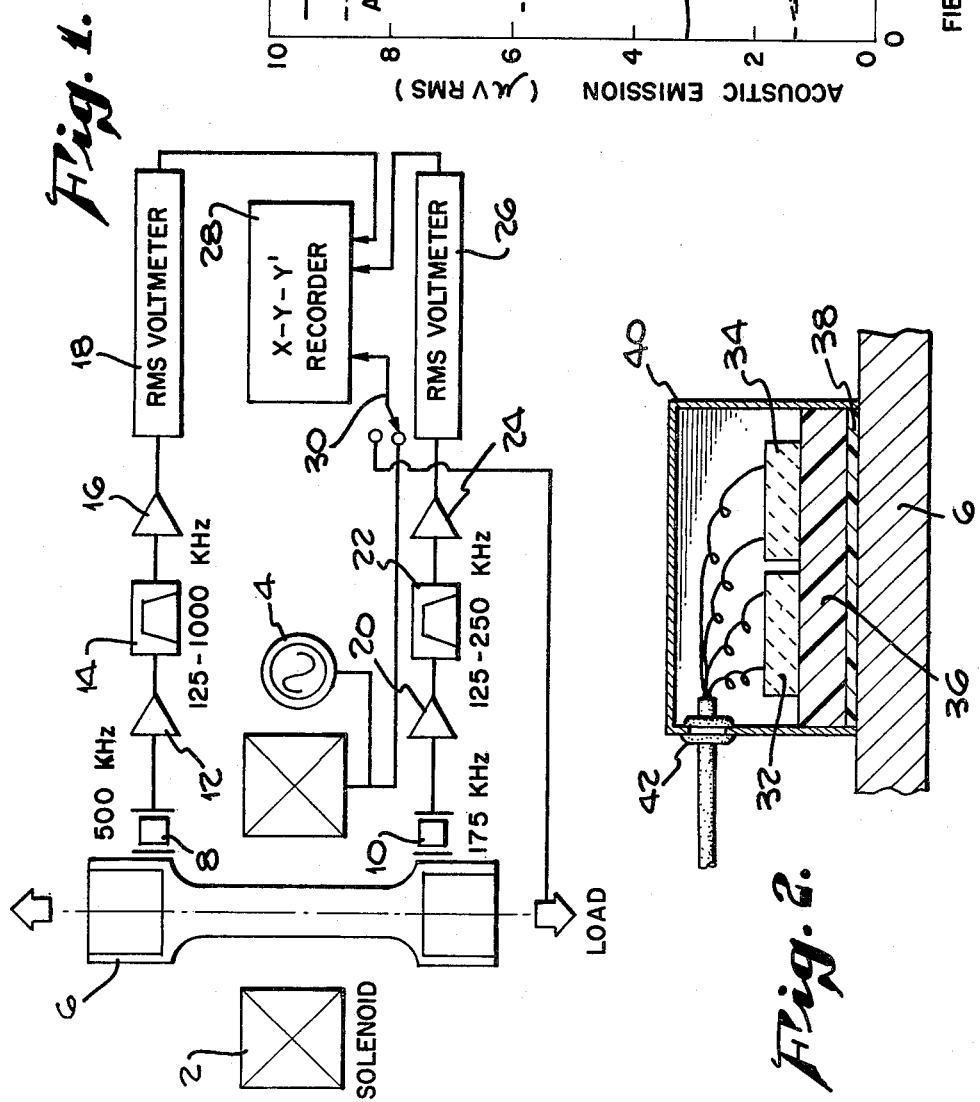
Fig. 1.
Fig. 2.
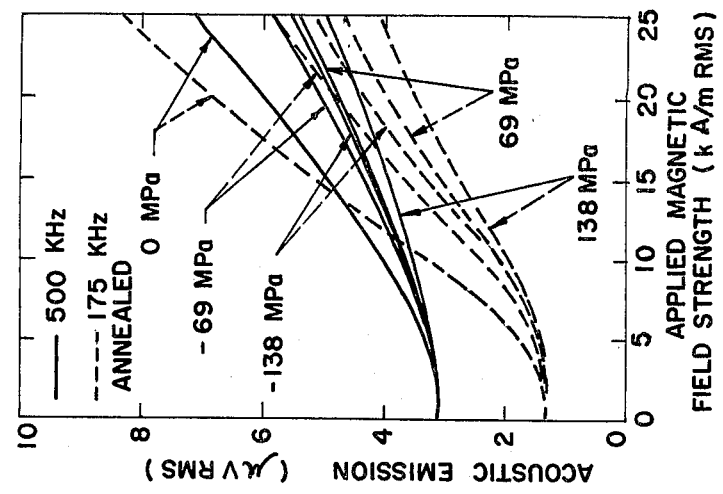
Fig. 3.

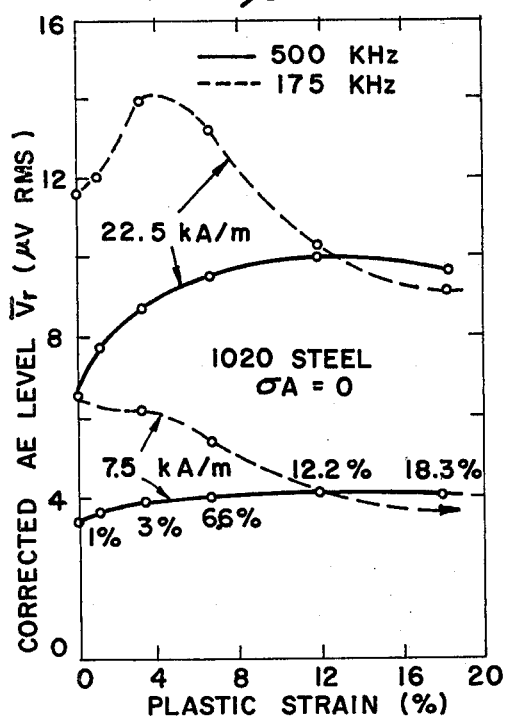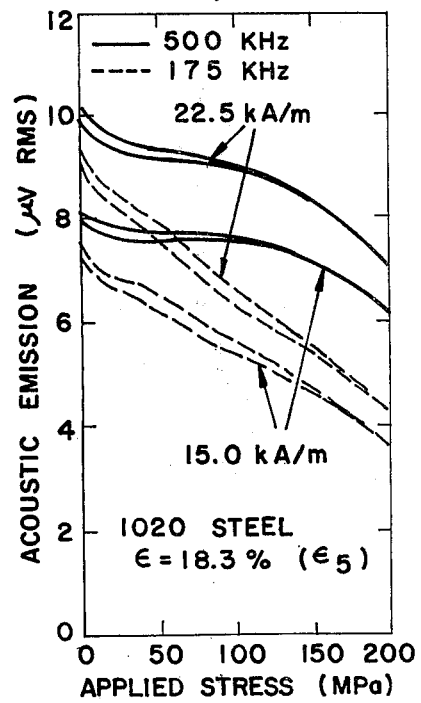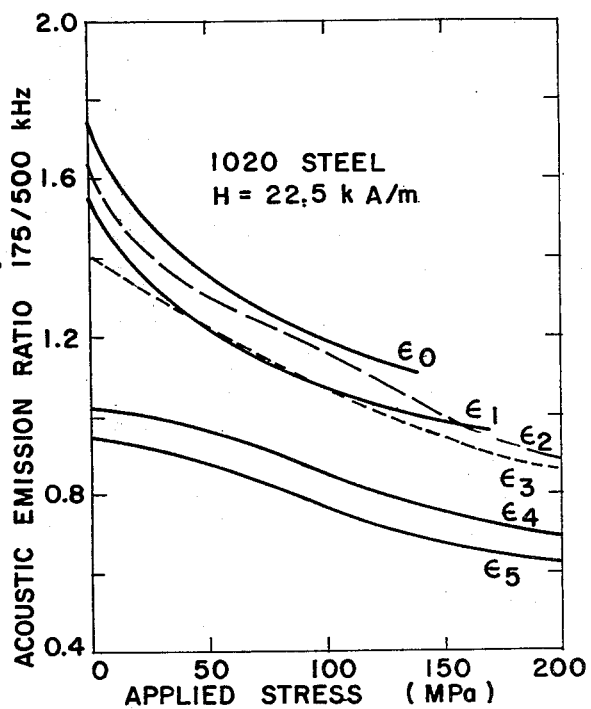

METHOD AND APPARATUS FOR ANALYZING SELECTED MATERIAL PROPERTIES WITH MAGNETOMECHANICAL ACOUSTIC EMISSIONS

The Government has rights in this invention pursuant to contract No. N00014-75-C-0419 awarded by the Office of Naval Research.

BACKGROUND OF THE INVENTION

1. Field of the Invention

This invention relates to the analysis of materials, and more particularly to a method and apparatus for analyzing selected properties of a ferromagnetic material by applying an alternating magnetic field to the material, and analyzing the resulting acoustic emissions induced in the material.

2. Description of the Prior Art

It is known that ferromagnetic materials will emit acoustic radiation when brought into an alternating magnetic field. This property has been used in various nondestructive testing techniques, such as the investigation and verification of structural integrity, and the detection and location of cracks and other structural flaws. A summary of the history and applications of acoustic emission work for both ferromagnetic and other materials is provided in Volume XI, Physical Acoustics Principles and Methods, edited by Warren P. Mason and R. N. Thurston, Academic Press, 1975, Chapter 6 (by Arthur E. Lord, Jr.).

Various properties of a ferromagnetic specimen will affect its acoustic emission response to an applied magnetic field. These properties include the stress to which the specimen is presently subjected or has been subjected in the past; strain or plastic deformation; the material's microstructure, which can be effected by various types of heat treatment; and chemical variations, such as differences in the carbon content of the specimen under investigation as compared to similar specimens. It has been suggested that acoustic emissions offer a method for measurement of at least some of these properties. For example, in a paper by Hideo Kusanagi, Hideo Kobayashi, and Hiroaki Sasaki originally published in Japanese and entitled "AE Characteristics and Stress Dependancy of Magnetization Process of Ferromagnetic Materials," published in "The Proceedings of the First National Conference on Acoustic Emission," held December 1977 Tokyo, Japan, pages 157-162, it was suggested that the stress dependancy of magnetically induced acoustic emissions could be utilized as a stress measurement. The authors recognized, however, that an instrumentation problem is existed in the measurement of acoustic emission intensity because of the effects of varying contact conditions between the sample and the acoustic emission transducer.

In addition to this instrumentation problem, there are other limitations on the use of acoustic emissions for measuring the properties of ferromagnetic materials. First, there is a fairly large degree of uncertainty, perhaps in the order of ten percent, in comparing a measured level of acoustic emissions to what has previously been determined to be a standard response curve. In other words, because of variations in the testing environment and between samples, it cannot be said that a given level of induced acoustic emissions in a sample can be related to a standard curve relating acoustic emissions to stress for the sample material, to exactly determine the stress on the sample. Also, because a variety of factors other than stress can affect the acoustic emission response of a given sample, there is no certainty that, for a given value of acoustic emission generated in response to a particular level of magnetization, a unique level of stress or other property has been determined.

Furthermore, in certain cases when the acoustic emission response is plotted over a range of values for a given property such as stress, the same acoustic emission level can correspond to more than one stress level. Accordingly, there may be an ambiguity in the significance of the acoustic emission level. On the other hand, in some situations the level of acoustic emissions will vary only slightly or not at all over a significant portion of the range of property values. This makes the significance of the acoustic emission level somewhat vague in that area, since it might correspond to any one of the property values within such portion of the range.

There is accordingly a continuing need for a method and apparatus which can utilize the significant amount of information available in magnetically induced acoustic emissions from ferromagnetic materials, but which are more accurate and reliable than those presently available.

SUMMARY OF THE INVENTION

In view of the problems existing in the prior art, it is an object of this invention to provide a method and apparatus for employing magnetically induced acoustic emissions to measure various properties of ferromagnetic materials with greater accuracy, reliability and precision than is available with prior art techniques.

Another object is the provision of an acoustic emission method and apparatus for analyzing ferromagnetic materials which is capable of distinguishing between the mechanical stress, plastic deformation, microstructure and chemical composition properties of a sample material insofar as they affect acoustic emissions.

It is also an object of the invention to provide a method and apparatus of acoustic emission analysis capable of distinguishing between different levels of a given property of the material under investigation, when more than one or even a whole range of such quantities correspond to substantially a single level of acoustic emission.

A further object is the provision of such a method and apparatus, in which errors arising from contact variations between the sample being analyzed and the acoustic emission transducer are substantially reduced.

The above objects are realized in the present invention by the provision of a method and apparatus which measures the acoustic emission response of a sample material at a plurality of values of a selected response parameter, rather than at only one value as in the prior art. The selected response parameter is characterized by an acoustic emission response which, for each selected parameter value, varies over a range of the material property being analyzed in mutual nonlinearity with variations in the acoustic emission response over the same range for each of the other selected values of the response parameter. The mutual nonlinearity in acoustic emission responses for the different response parameter values significantly increases the useful information that can be attained, and is employed by comparing the measured acoustic emission responses to each other and to standards for the selected property and response parameter values. The result is to substantially reduce the tolerances, ambiguities and vagueness associated with prior art measurement techniques.

In the preferred embodiment the selected response parameter employed is the frequency of the acoustic emission response; the signal threshold level for obtaining an acoustic emission count rate or the magnetic field strength may also be used. The subject invention is applicable to the measurement of material properties such as stress, plastic deformation, microstructure and chemical composition.

The invention also contemplates a significant reduction in errors arising from contact problems between the material sample and the acoustic emission transducer. A unitary means, such as a layer of acoustic transmitting material, couples the sample to different transducers corresponding to different acoustic emission measurent frequencies, or to a single transducer having means to measure acoustic emissions at a plurality of frequencies. Any measurement errors at one frequency will tend to be cancelled by the effects of a corresponding measurement error at the other frequencies.

To determine the value of the property being measured, either the absolute value of the acoustic emission responses for the selected response parameter values, the ratio between the responses, or both absolute values and ratios are measured and compared to standard acoustic emission responses for corresponding values of the selected response parameter.

These and other advantages and features of the invention will be apparent to those skilled in the art from the following detailed description, in conjunction with the accompanying drawings, in which:

DESCRIPTION OF THE DRAWINGS

FIG. 1 is a schematic diagram of a system for applying an alternating magnetic field to a material being analyzed, and for detecting acoustic emissions from the material;

FIG. 2 is a cross-sectional elevation view of a dual frequency transducer constructed in accordance with the invention;

FIG. 3 is a graph relating acoustic emission levels induced in a ferromagnetic material at 500 kHz and 175 kHz, to applied magnetic field strength and stress levels;

FIGS. 8 and 9 are graphs relating 500 kHz and 175 kHz acoustic emission levels to applied stress for 1020 steel with respectively zero and non-zero initial strains, at two different magnetization levels;

FIG. 10 is a graph relating 500 kHz and 175 kHz acoustic emission levels to initial strain levels for 1020 steel with zero applied stress, at two different magnetization levels;

FIG. 11 is a graph, derived from information of the type shown in FIGS. 8–10, relating the ratio between acoustic emissions at 500 kHz and 175 kHz to applied stress for different levels of initial strain on 1020 steel;

DETAILED DESCRIPTION OF PREFERRED EMBODIMENTS

Measuring Apparatus and Procedures

Figure 5:
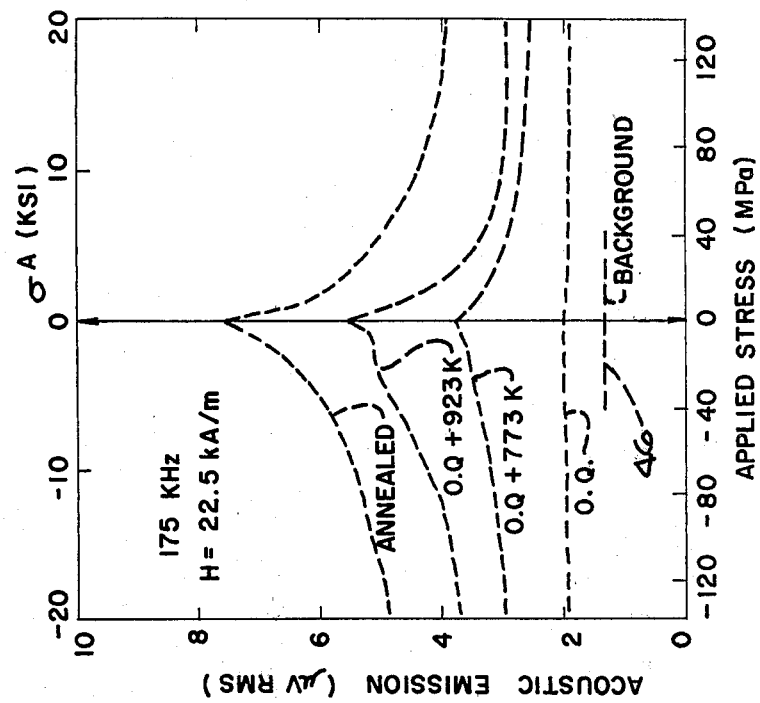
FIGS. 4 and 5 are graphs relating induced acoustic emission levels at a constant magnetic field strength, to applied stress and heat treatment at 500 kHz and 175 kHz, respectively.

Referring to FIG. 1, apparatus for measuring the acoustic emission response of a ferromagnetic material is shown schematically. An alternating magnetic field is set up by a solenoid 2 energized by a source of AC current 4. A specimen material 6 for which analysis is sought is placed within the magnetic field so that acoustic emissions are induced within the specimen under the influence of the field. While the specimen 6 is shown as being encircled by solenoid 2, such an arrangement may not be possible for work in the field, such as the testing of portions of railroad track. For such applications, a magnetic field source may be brought into contact with the specimen along one of its sides.

The testing apparatus shown is designed to detect acoustic emissions induced in the specimen at two different emission frequencies. The frequency at which the acoustic emissions are measured are referred to herein as a response parameter, meaning a physical property whose value determines the characteristics of the specimen's acoustic emission response. Other response parameters discussed herein are the signal threshold level for obtaining an acoustic emission count rate, and the magnetic field strength.

In accordance with the invention, it has been found that the measurement of acoustic emission response at a plurality of selected values of one or more such response parameters enables an improved analysis of various properties of the specimen, where the acoustic emission responses for different values of a given parameter vary in mutual nonlinearity as the level of the analyzed property varies. Because of this nonlinearity, the results of testing at two different values of the response parameter can be compared and used to substantially reduce or eliminate vagueness, ambiguity or high error tolerances associated with the test results from either of the parameter values by themselves.

Continuing with FIG. 1, a pair of transducers 8 and 10, each adapted to translate acoustic emissions at a particular frequency to an electrical signal, are connected to opposite ends of specimen 6. Transducers 8 and 10 have nominal center response frequencies of 500 and 175 kHz, respectively. Transducer 8 is connected in series with a preamplifier 12, a band pass filter 14 with a range of 125–1000 kHz, and an output amplifier 16, to a voltmeter 18 adapted to measure RMS voltage. Transducer 10 is connected to a similar circuit consisting of preamplifier 20, 125–250 kHz band pass filter 22, amplifier 24 and RMS voltmeter 26.

The voltmeter outputs are each connected to an X-Y-Y' recorder 28 which is capable of selecting between the two voltages for controlling one axis of a plot. The other axis of the plot is controlled by an input along lead 30 representing either the magnetic field strength created by solenoid 2, as shown, or by the value of a load such as the mechanical stress applied to specimen 6.

A more detailed view of an alternate transducer arrangement is shown in FIG. 2. In this arrangement, a pair of piezoelectric transducer elements 32 and 34, each responsive to selected acoustic emission frequencies, are coupled to the specimen 6 by a unitary coupling device which eliminates discrepancies between readings from the two transducers. Such discrepencies might result for example, from the different positions of the transducers of FIG. 1 along the specimen, or from differences between the apparatus coupling each transducer to the specimen. As shown, transducer elements 32 and 34 are placed side-by-side in close proximity to each other, on a single epoxy shoe 36. Shoe 36 in turn is held to specimen 6 by an acoustic layer 38 such as viscous resin or glue. Layer 38 forms the bottom portion of a housing 40 for the above-described elements. Electrical connections to transducers 32 and 34 are provided through a bushing 42 in the housing wall.

Transducer elements 32 and 34 are thus acoustically coupled to specimen 6 through a unitary coupling medium, consisting of epoxy shoe 36 and coupling layer 38, which provide a common acoustical interface for each of the elements 32 and 34. In this manner spurious differences in the acoustic emissions detected by the two transducer elements, resulting from imperfections in the measuring apparatus, are substantially eliminated; any differences in the two measured levels of acoustic emission will be due substantially solely to the differences in the respective response frequencies of the transducers. Other arrangements for eliminating equipment imperfections from the relative measurements of acoustic emissions can also be envisioned, such as the use of a single piezoelectric element with two resonant frequencies, or stacking two elements rather than placing them side-by-side.

Stress-Microstructure Analysis

FIGS. 3–6 show the results of investigations which related applied stress and microstructure, as determined by heat treatment, to acoustic emissions at 500 kHz and 175 kHz. The specimens investigated consisted of steel railroad wheel samples having the following non-ferric components;

| Element | Percentage |
|---|---|
| C | 0.74 |
| Mn | 0.68 |
| Si | 0.27 |
| P | 0.018 |
| S | 0.040 |
| Cr | 0.16 |

| Element | Percentage |
|---|---|
| Ni | 0.15 |
| Mo | 0.03 |
| Cu | 0.15 |

The wheel samples were annealed at 1173° K. for one hour and furnace cooled. Some of the samples were also oil-quenched after austenitizing at 1173° K. for one hour, and some of the oil-quenched samples were also tempered at either 773° K. or 923° K. for one hour and air cooled. Annealed samples were found to be fully pearlitic, whereas the oil-quenched samples were martensitic. Following heat treatment and cleaning, transducers for acoustic emission detection were attached to the flat ends, as illustrated in FIG. 1.

Referring now to FIG. 3, the acoustic emission responses of the annealed sample at 500 kHz and 175 kHz is shown for various values of magnetic field strength and applied stress. Acoustic emission is represented in terms of RMS microvolts, magnetic field strength in RMS kiloamperes per meter, and applied stress in mega pascals. Positive and negative stress values indicate compression and tension, respectively.

From an inspection of FIG. 3 it can be determined that, for a given magnetic field strength, the acoustic emission responses at the two response frequencies vary in mutual nonlinearity over the range of stress values shown. For example, with a field strength of 22.5 kA/m the acoustic response for zero stress is greater at 175 kHz than at 500 kHz, whereas the acoustic responses at plus or minus 69 or 138 mpa is greater at 500 kHz than at 175 kHz. Thus, by measuring and comparing the acoustic emission responses at the two frequencies rather than at only one frequency as in the prior art, more useful information can be obtained to determine the stress level of the specimen.

An alternate presentation to that shown in FIG. 3 is to plot acoustic emissions at specified frequencies against applied stress for given magnetic field strengths and microstructures. Such a presentation is made in FIGS. 4 and 5, which plot the acoustic emissions at 500 kHz and 175 kHz, respectively, against applied stress at a magnetic field strength of 22.5 kA/m. Annealed, oil-quenched, and oil-quenched samples tempered respectively at 773° K. and 923° K. are shown. Again, the results at the two frequencies are mutually nonlinear, the slopes of the curves for 175 kHz generally being greater than for 500 kHz, especially at the lower stress levels. Furthermore, the acoustic emission responses at the two frequencies are observed to vary in a mutually dissimilar manner for the different microstructures resulting from the different heat treatments. At 175 kHz the annealed sample displayed the greatest acoustic emission response throughout the entire range of stress levels, followed in order by oil-quenched with tempering at 923° K., oil-quenched with tempering at 773° K., and oil-quenched with no tempering. At 500 kHz, by contrast, the annealed sample and the oil-quenched samples tempered at 773° K. alternated in greater acoustic emission response at different portions of the stress range, followed in order by oil-quenched tempered at 923° K., and oil-quenched with no tempering.

Figure 4:
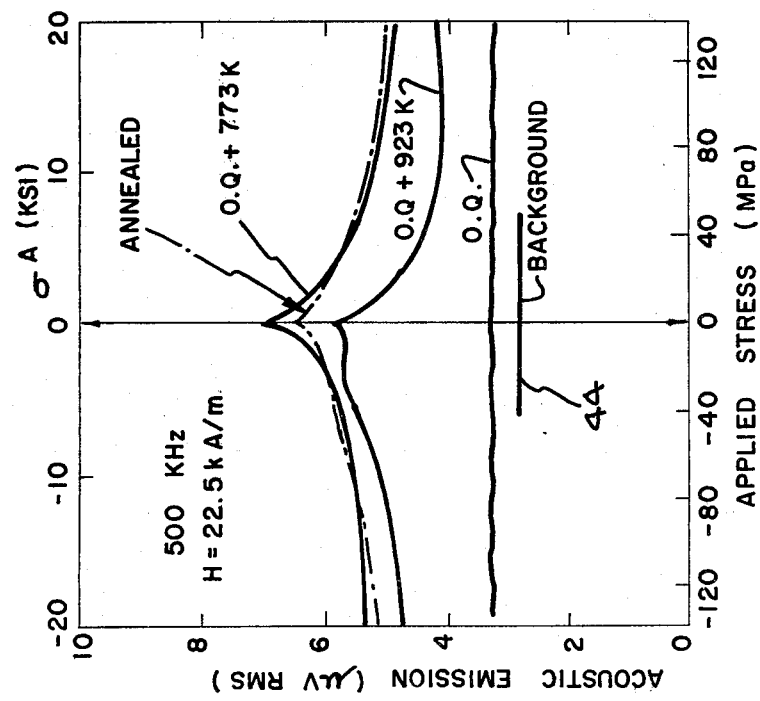

Based upon this observed nonlinearity in the acoustic emission response at different frequencies, an added dimension of certainty in the results of a test can be obtained by taking measurements at two or more frequencies, and comparing the measured acoustic emission values at each frequency to each other and to standard acoustic emission responses such as those illustrated in FIGS. 4 and 5. Nominally, the stress on a specimen may be determined by observing its acoustic emission response at a specified frequency, and comparing the response to a standard response pattern such as those illustrated in FIGS. 4 and 5 to obtain the corresponding stress value. Assuming this determination involves a given error tolerance, the effective error tolerance can in most cases be reduced by observing the acoustic emission response at a plurality of selected frequencies, calculating the range of possible stresses within the error tolerance at each frequency, and narrowing the final stress calculation to the mutually overlapping portions of the tolerance bands at each frequency.

Figure 6:
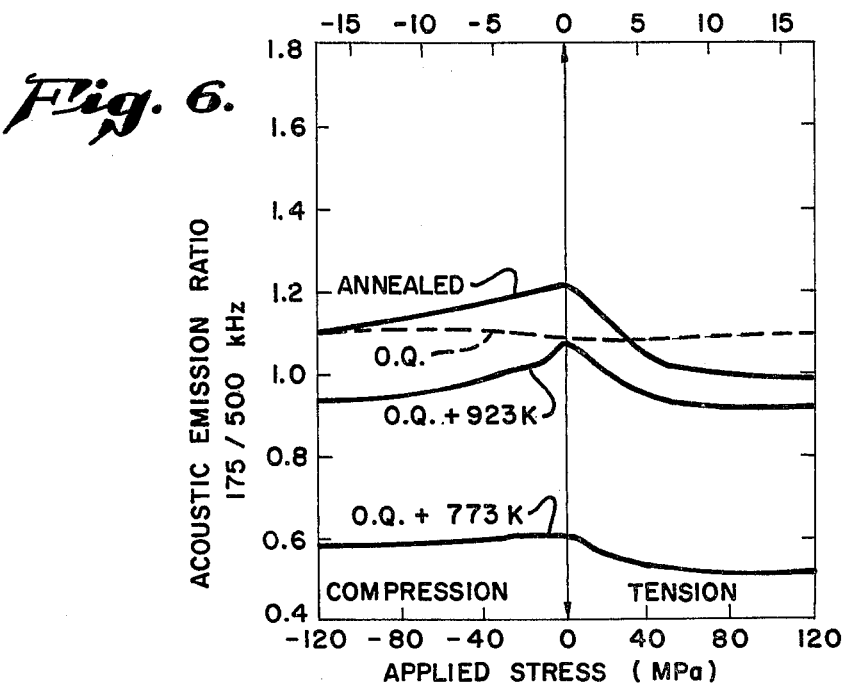
FIG. 6 is a graph showing the ratio between the induced acoustic emission levels of FIGS. 4 and 5.

A preferred way of comparing the observed acoustic emission responses at different frequencies is to calculate the ratio between the observed responses, and to compare the calculated ratio to a standard response ratio such as that shown in FIG. 6. This figure comprises a plot of the ratio of the 175 kHz standard response of FIG. 5 to the 500 kHz standard response of FIG. 4, after correcting for the different background noise levels identified by lines 44 and 46 of FIGS. 4 and 5, respectively. The background noise correction is based upon the conventional assumption that the mean-square voltage output equals the sum of the mean-square voltages of signal and noise. Thus, the corrected voltages representing the measured acoustic emissions are obtained by taking the square root of the difference between the square of the measured voltage, and the square of the background noise voltage, in RMS values.

The ratio between measured acoustic emissions for a test specimen can be compared to standard ratios, such as those shown in FIG. 6 to more accurately determined the stress on the specimen. In certain situations, such as when the slope of the two-frequency ratio response graph is steeper than the slope of the response graph for a single frequency, or the same acoustic emission value corresponds to multiple stress values for the single frequency graph but to only a unique stress value for the ratio graph, the ratio graph by itself can give a more precise indication of stress. In general, the ratio graph can be used in combination with a standard single frequency graph to produce a more precise stress measurement than is achievable with a standard single frequency graph by itself. Acoustic emission responses are taken at two frequencies, the ratio between the responses is calculated, and both the individual responses and the response ratio are compared to corresponding standard response graphs to determine stress range that would satisfy all three graphs for the measured levels of acoustic emissions and their assumed error tolerances.

The acoustic emission ratios discussed above can be used in combination with the absolute values of the acoustic emissions to identify applied or residual stress prior to cold working and microstructural changes, or for a defined microstructure. Alternately, the technique can be applied to detect microstructural changes themselves. For example, the multifrequency approach may be utilized for the detection of inadvertently produced martensite regions in railroad wheels. While residual stress affects the acoustic emission level significantly, the martensite produces a very large decrease in the acoustic emission level, so that its presence can be readily be detected.

Stress-Strain Analysis

FIGS. 7–13 illustrate the application of the invention to the analysis of plastic deformation, or strain. Results with two specimens are shown, one specimen consisting of AISI 1020 steel and the other of a low alloy steel, ASTM A533B, Class 2. Stress-strain diagrams for these materials are given in FIG. 7. Acoustic emission measurements were taken at the strain levels indicated for each specimen.

Figure 8:
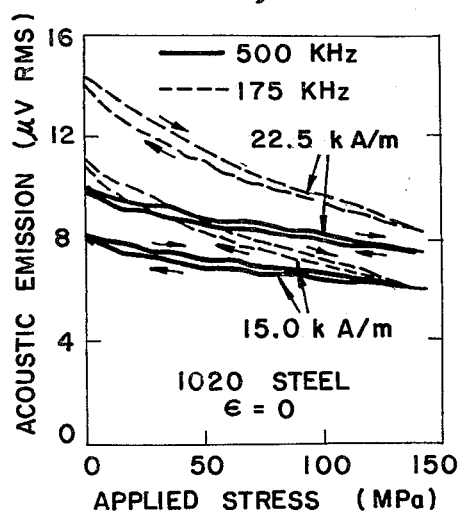

FIG. 8 is a graph showing the level of acoustic emissions produced by magnetic field strengths of 22.5 and 15.0 kA/m, at 500 and 175 kHz, with zero initial strain. It will be noted that a certain amount of hysterisis was present as stress was first applied and then removed. FIG. 9 is similar to FIG. 8, but shows the results of stressing the 1020 steel specimen with an initial strain of 18.3 percent. It can be seen again that the acoustic emission response varies significantly with the frequency at which the response is measured, and is also dependent upon the strain level. Furthermore, it can be seen that the acoustic emission response is also dependent upon the magnetic field strength. Thus, while the ensuing discussion is directed to the use of frequency as a response parameter for analyzing the stress or strain characteristics of the specimens, it would also be possible to use magnetic field strength as the response parameter instead of frequency.

A comparison of FIGS. 8 and 9 reveals that, as the 1020 steel sample was progressively deformed and its acoustic emission response measured, there are several significant differences in the responses when viewed in terms of either the frequency or field strength response parameters. For example, throughout the range of applied stresses, greater acoustic emissions were induced at 175 kHz than at 500 kHz for either field strength with zero initial strain, whereas the opposite was true for the same field strengths at a strain of 18.3 percent. Also, the shapes of the individual curves varied significantly at the two strain levels. Thus, a greater capability for detection of stress and/or strain is offered when measurements of a sample are taken at a plurality of levels of a given response parameter and compared to standard responses such as those illustrated in FIGS. 8 and 9. The comparison is accomplished in a manner similar to that for the stress-microstructure relationships of FIGS. 4–6, described above. Where an individual curve is approximately flat, such as in the vicinity of 100 mpa for the 500 kHz, 15.0 kA/m curve of FIG. 9, the use of a plurality of response parameters is particularly helpful in obtaining a more precise stress measurement.

FIG. 10 illustrates the acoustic emission responses obtained with zero applied stress, and initial plastic strains as indicated along the horizontal axis. By taking similar measurements at the particular stress and strain levels indicated on FIG. 7, and calculating the ratio of the acoustic emissions at 175 kHz to the emissions at 500 kHz, standard ratio response curves for the various strain levels can be obtained as shown in FIG. 11. This figure is similar to FIG. 6 in that it provides response ratios for one selected property of the specimen being analyzed (applied stress) in terms of another selected property (microstructure in FIG. 6 or strain in FIG. 11), at two levels of a selected response parameter (acoustic emission frequency).

Figure 7:
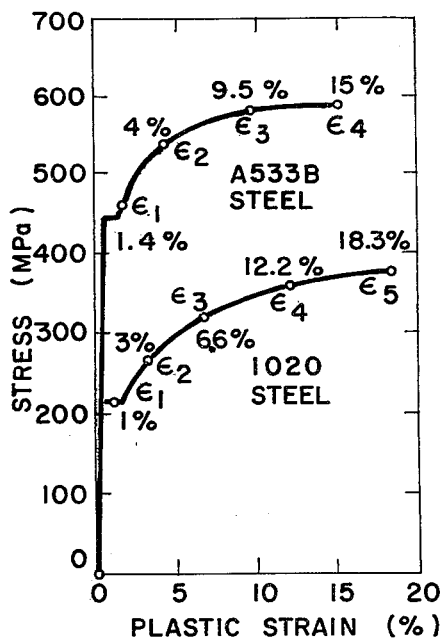
FIG. 7 is a stress-strain diagram showing the strain levels at which the acoustic emission measurements of FIGS. 8–13 were made.
Figure 12:
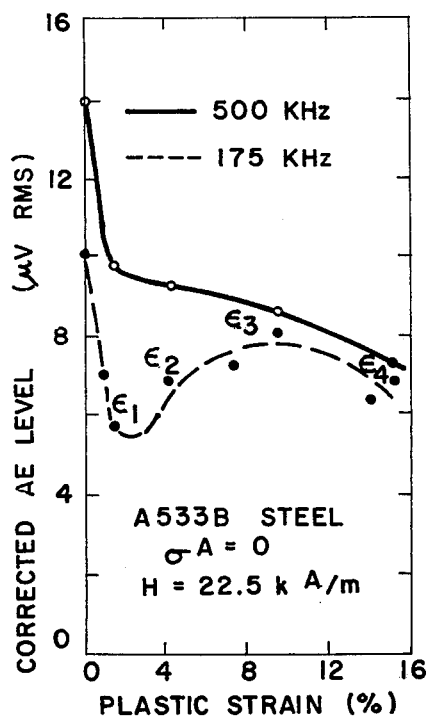
FIG. 12 is a graph, similar to FIG. 10, relating 500 kHz and 175 kHz acoustic emission levels to initial strain levels for A533B steel.
Figure 13:
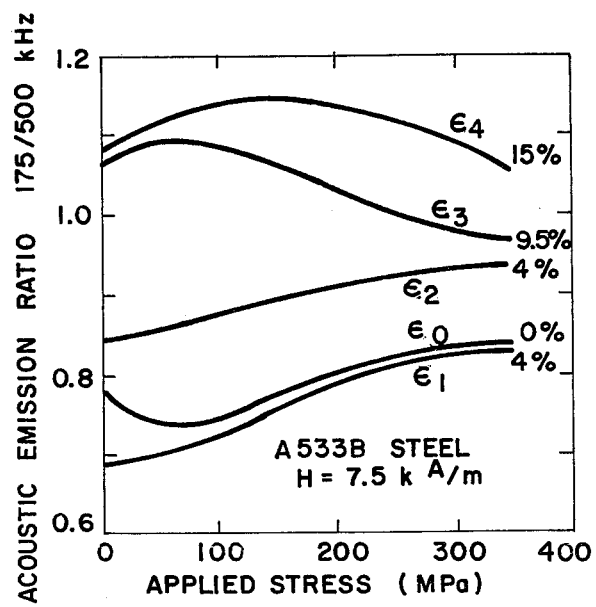
FIG. 13 is a graph, similar to FIG. 11, relating the ratio between acoustic emissions at 500 kHz and 175 kHz to applied stress for different levels of initial strain on A533B steel.

FIGS. 12 and 13 are similar to FIGS. 10 and 11, respectively, showing the acoustic emissions and response ratios obtained with ASTM A533B steel at a field strength of 22.5 kA/m for FIG. 12, and 7.5 kA/m for FIG. 13. Again, the use of multiple values of the frequency response parameter permits a more precise analysis of stress or strain. The values for these curves were obtained from readings taken at the indicated points on the A533B stress-strain curve FIG. 7.

Stress-Chemical Composition Analysis

Figure 14:
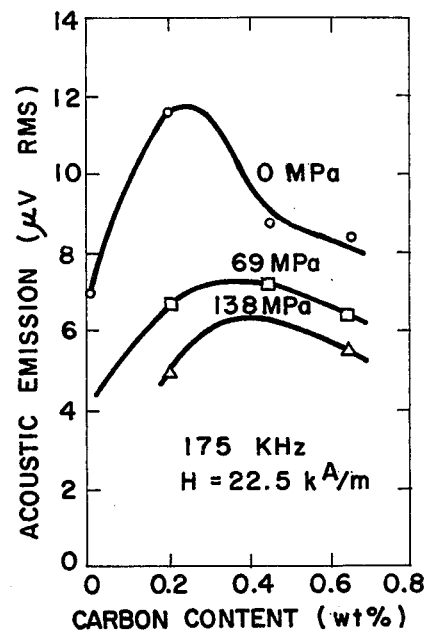
FIGS. 14 and 15 are graphs relating acoustic emissions at 175 kHz and 500 kHz, respectively, to the carbon content of iron and steel, for three different applied stress levels.
Figure 17:
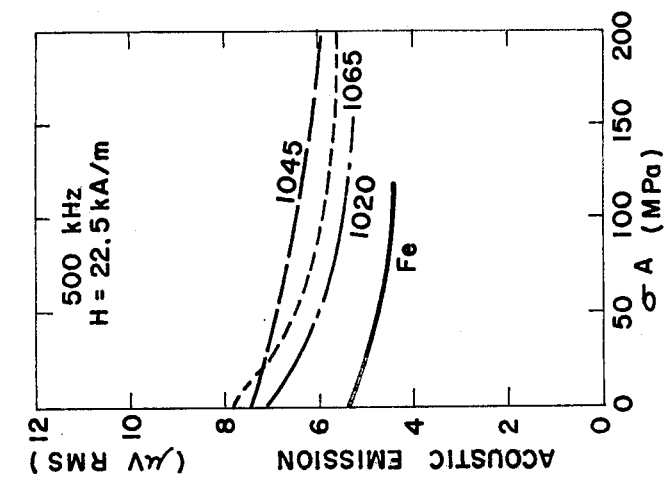
FIGS. 16 and 17 display information of the type given in FIGS. 14 and 15, respectively, in a different format consisting of graphs relating acoustic emissions at 175 kHz and 500 kHz, respectively, to applied stress for four-different iron and steel compositions.
Figure 16:
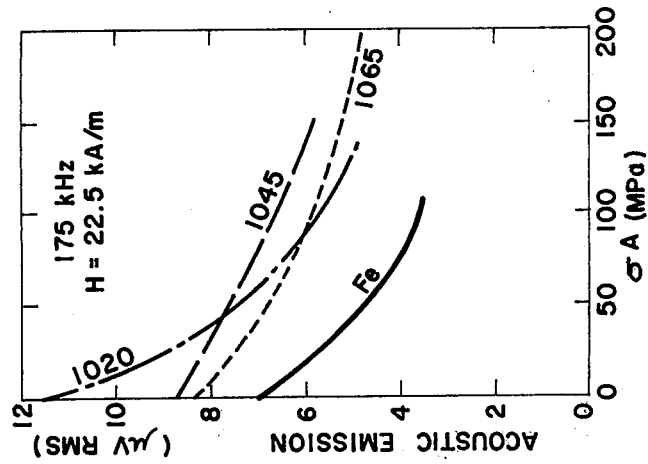
Figure 15:
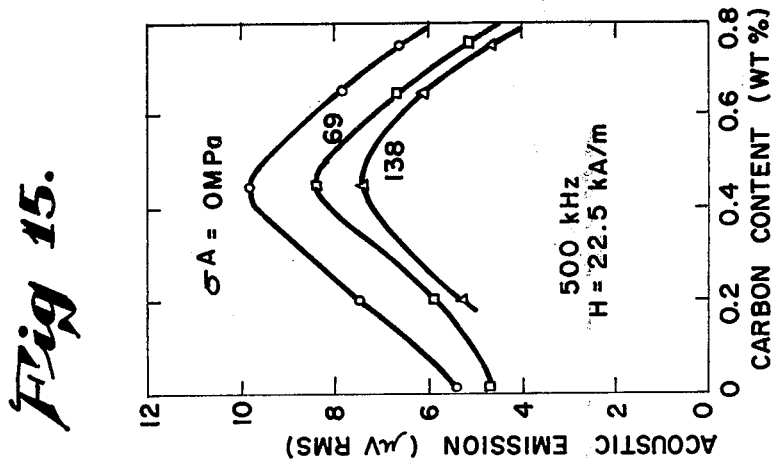

FIGS. 14–18 illustrate the principles of the invention applied to the analysis of stress and chemical composition for various ferromagnetic materials. In the examples shown, standard response curves were obtained by taking acoustic emission measurements at 175 kHz and 500 kHz for the following four materials: iron, 1020 steel (0.2 percent carbon), 1045 steel (0.45 percent carbon), and 1065 steel (0.65 percent carbon). The results of the measurements for three different stress levels are shown in FIGS. 14 and 15 for 175 and 500 kHz, respectively. In these figures, acoustic emissions are plotted against carbon content. This type of information can also be plotted as shown in FIGS. 16 and 17, in which acoustic emissions are plotted against stress for various chemical contents at 175 kHz and 500 kHz, respectively. Either type of presentation can function as a standard response against which unknown specimens can be tested, depending upon which of the two properties, stress of chemical content, it is desired to analyze.

Figure 18:
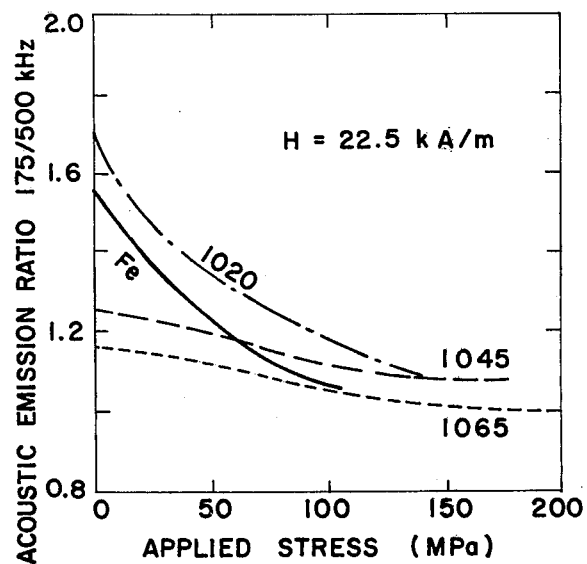
FIG. 18 is a graph, derived from information of the type shown in FIGS. 14–17, relating the ratio between acoustic emissions at 500 kHz and 175 kHz to applied stress for four different iron and steel compositions.

Again, the critical aspect is that standard response curves and measurements of the specimen being analyzed are obtained at a plurality of different values of the selected response parameter, in this case acoustic emission frequency. By comparing the measured responses at each frequency to the established standard responses and to each other, a more precise indication of either stress or chemical content may be obtained. FIG. 18 shows the ratio between the standard response curve of FIGS. 16 and 17, and may be employed in conjunction with those curves to obtain a more precise indication of stress. Alternatively, if carbon content rather than stress is to be measured, the standard curves of FIGS. 14 and 15 could be compared to obtain ratio curves for chemical content.

Threshold Count Rate Response Parameter

Thus far, the use of acoustic emission frequency as the selected response parameter for acoustic emission measurements has been illustrated, and the use of magnetic field strength as the response parameter has been indicated. Another response parameter that could be usually employed is the signal threshold level used to obtain an acoustic emission count rate. The term "count rate" as used herein refers to the number of acoustic emissions obtained per second with an amplitude in excess of a selected threshold level. Where the acoustic emission count rate varies nonlinearly for different values of a selected ferromagnetic material property as the count rate threshold varies over a given range, the count rate threshold may be used as a response parameter for measurements of that property in a manner similar to the use of different response frequencies, as discussed above.

Figure 19:
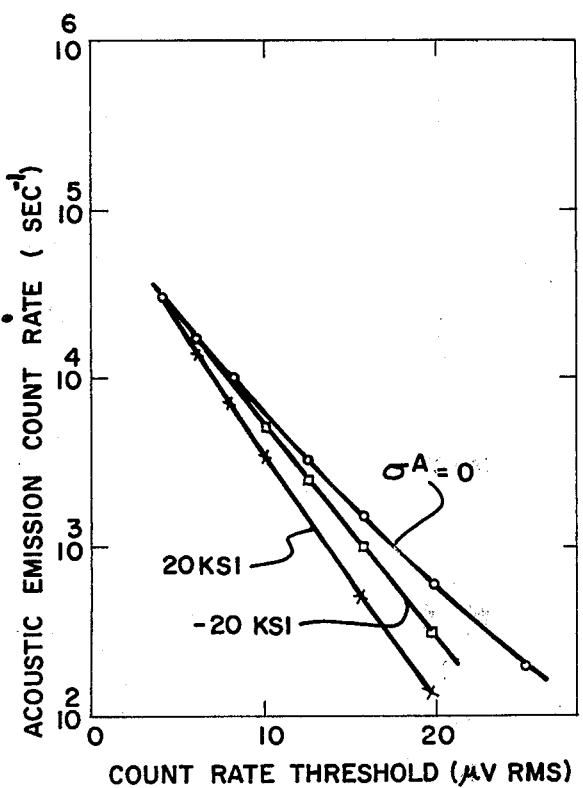
FIG. 19 is a graph relating the count rate of 175 kHz acoustic emissions induced in A533B steel to the count rate threshold level, for three different levels of applied stress.

FIG. 19 shows an example of a situation in which the count rate threshold can be employed as the selected response parameter. Acoustic emission count rates are plotted on a vertical logarithmic scale against the square of the normalized count rate threshold value. The standard responses shown were obtained from a specimen of A533B steel at three different stress levels. It can be seen that the count rates vary with stress level. By taking measurements at numerous different stress levels for specified count rate threshold values, standard response curves plotting count rate against stress could be obtained for those threshold values. The standard response curves for given pairs of threshold values could then be compared to establish standard response ratio curves.

Analysis of a test specimen would proceed by taking count rate measurements for each of the selected threshold levels, and comparing the results at each threshold level to each other and to the standard curves. In this manner, the stress to which the specimen is subjected can be determined with greater accuracy than if measurements and a standard response were provided at only a single threshhold level.

While various embodiments of the invention have been illustrated and described, it should be understood that numerous modifications and improvements are possible within its scope. For example, the data presented in FIG. 19 was acquired by varying the gain on an acoustic emission signal processor. It is possible to utilize a pulse-height analyzer often employed in nuclear physics studies, to acquire the entire amplitude distribution spectrum. With the aid of such apparatus, it may become practical to employ the amplitude distribution of induced acoustic emission as a response parameter. Accordingly, the invention should be limited only in terms of the appended claims.

I claim:

1. A method of analyzing a selected property of a ferromagnetic material, said property influencing the acoustic emission response of the material to an applied alternating magnetic field, comprising the steps of:
    applying an alternating magnetic field to the material,
    measuring the acoustic emission response of the material, using a plurality of individual transducers each responsive to a single frequency, at a selected response parameter, said selected response parameter being characterized by an acoustic emission response which, for each of said selected response parameter values, varies over a selected range of the analyzed property in mutual nonlinearity with variations in the acoustic emission response over the same range for each of the other selected response parameter values, and
    comparing the measured acoustic emission responses to each other and to standard acoustic emission responses for said selected property and response parameter values.

2. The method of claim 1, wherein the selected response parameter is the RMS voltage of the acoustic emission response.

3. The method of claim 1, wherein the selected response parameter is the signal threshold level for obtaining an acoustic emission count rate.

4. The method of claim 1, wherein the selected response parameter if the magnetic field strength.

5. The methods of claims 1, 2, 3 or 4, wherein the selected property being analyzed is selected from the group consisting of: stress, plastic deformation, microstructure and chemical composition.

6. The method of claim 1, wherein said comparison step includes determining the ratio between the measured acoustic emission responses for the selected response parameter values, and comparing said ratio to standard acoustic emission response ratios for those response parameter values.

7. The method of claims 1 or 6, wherein the absolute values of the acoustic emission responses for the selected response parameter values are measured and compared to standard acoustic emission responses for those response parameter values.

8. A method of analyzing a selected property of a ferromagnetic material, said property influencing the acoustic emission response of the material to an applied alternating magnetic field, comprising the steps of:
applying an alternating magnetic field to the material,
measuring, with a plurality of transducers each responsive to a single selected frequency, the acoustic emission response of the material at each of said plurality of single selected frequencies, and
comparing the measured acoustic emission responses to each other and to standard acoustic emission responses for the selected property and frequencies.

9. The method of claim 8, wherein the absolute value of the measured acoustic emission response at each single selected frequency is measured and compared to a standard acoustic emission response for that frequency.

10. The method of claims 8 or 9, wherein said comparison step includes determining the ratio between the acoustic emission responses at the selected frequencies, and comparing said ratio to standard acoustic emission response ratios for those frequencies.

11. The method of claim 8, wherein a count rate for the acoustic emission response at each selected frequency is measured and compared to a standard acoustic emission count rate for that frequency.

12. The method of claim 11, wherein the ratio between the acoustic emission count rates at the selected frequencies is measured and compared to a standard acoustic emission count rate ratio for those frequencies.

13. The methods of claims 8 or 11, wherein the measured acoustic emission responses are compared to standard acoustic emission responses isolating one or more of the following selected properties: stress, plastic deformation, microstructure and chemical composition.

14. Means for analyzing a selected property of a ferromagnetic material, said property influencing the acoustic emission response of the material to an applied alternating magnetic field, comprising:
means for applying an alternating magnetic field to the material, and
a plurality of transducer means for simultaneous measuring, at a single frequency preselected for each transducer means, the acoustic emission response of the material at a selected response parameter, said selected response parameter being characterized by an acoustic emission response which, for each of said selected parameter values, varies over a selected range of the analyzed property in mutual nonlinearity with variations in the acoustic emission response over the same range for each of the other selected response parameter values.

15. The analyzing means of claim 14, wherein the selected response parameter comprising the RMS voltage of the acoustic emission response.

16. The analyzing means of claim 15, unitary means for acoustically coupling said plurality of transducer means to the material to be analyzed, said unitary means proving a common acoustical interface with the material for said transducer means.

17. The analyzing means of claim 16, said analyzing means including a housing, said transducer means being held within said housing, and unitary layers of acoustic transmitting material having a first surface adapted to contact a material to be analyzed, and a second surface coupled to transmit acoustic emissions to said transducer means.

18. The analyzing means of claim 14, wherein the measuring means comprises means for measuring, for each of a plurality of threshold levels, the acoustic emission count rate of the material above said threshold level, and means for varying the threshold level among said plurality of levels.

19. The analyzing means of claim 18, wherein said plurality of threshold levels comprises a substantially continuous range of threshold levels.

20. A method of analyzing a selected property of a ferromagnetic material, said property influencing the acoustic emission response of the material to an applied alternating magnetic field, comprising the steps of:
applying an alternating magnetic field to the material,
controlling the acoustic emission response of the material by use of two or more transducers each responsive to a single preselected frequency,
measuring the acoustic emission response of the material at each of a plurality of selected values of a selected response parameter, and
comparing the measured acoustic emission responses to each other and to standard acoustic emission responses for the selected property and response parameter values.

21. The method of claim 20, wherein the selected response parameter is the magnetic field strength applied to the material.

22. The method of claim 20, wherein the selected response parameter is the magnetic field strength generated with the material in place for said measuring step.

23. The method of claim 20, wherein the selected response parameter is the RMS voltage response generated by the acoustic emission responses at said two or more preselected frequencies.

24. The method of claim 20, wherein the selected response parameter is the ratio of the RMS voltage responses generated by the acoustic emission responses at said two or more frequencies.

25. The method of claim 20, wherein the selected response parameter is the acoustic emission count rate.

26. The method of claim 20, wherein the selected response parameter is the ratio of the acoustic emission count rates.

27. The method of claim 20, wherein selected property being analyzed is selected from the group consisting of: stress, plastic deformation, microstructure and chemical composition.

* * * * *